(12) United States Patent
Grusendorf et al.

(10) Patent No.: US 8,927,782 B2
(45) Date of Patent: Jan. 6, 2015

(54) VAPOR SEPARATION IN ALCOHOL PRODUCTION

(75) Inventors: Gerald Grusendorf, Rosharon, TX (US); Victor J. Johnston, Houston, TX (US); David Lee, Seabrook, TX (US); Lincoln Sarager, Houston, TX (US); R. Jay Warner, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 669 days.

(21) Appl. No.: 13/197,740

(22) Filed: Aug. 3, 2011

(65) Prior Publication Data

US 2013/0032467 A1 Feb. 7, 2013

(51) Int. Cl.
*C07C 29/149* (2006.01)
*B01D 3/06* (2006.01)

(52) U.S. Cl.
CPC ............... *B01D 3/06* (2013.01); *C07C 29/149* (2013.01)
USPC ........................................................ 568/885

(58) Field of Classification Search
CPC ...................................................... C07C 29/149
USPC ........................................................ 568/885
See application file for complete search history.

(56) References Cited

U.S. PATENT DOCUMENTS

| | | | |
|---|---|---|---|
| 2,649,407 A | 8/1953 | Harrison et al. |
| 2,702,783 A | 2/1955 | Harrison et al. |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,990,952 A | 11/1976 | Katzen et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,520,213 A | 5/1985 | Victor |
| 4,541,897 A | 9/1985 | Sommer et al. |
| 4,569,726 A | 2/1986 | Berg et al. |
| 4,626,321 A | 12/1986 | Grethlein et al. |
| 4,678,543 A | 7/1987 | Houben et al. |
| 4,692,218 A | 9/1987 | Houben et al. |
| 4,804,791 A | 2/1989 | Kitson et al. |
| 4,842,693 A | 6/1989 | Wheldon |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |

(Continued)

FOREIGN PATENT DOCUMENTS

| | | |
|---|---|---|
| CN | 102091429 | 6/2011 |
| EP | 0104197 | 4/1984 |
| EP | 0167300 | 1/1986 |
| EP | 0456647 | 11/1991 |
| EP | 2060553 | 5/2009 |

(Continued)

OTHER PUBLICATIONS

International Search Report and Written Opinion for PCT/US2011/046488 mailed Sep. 27, 2012.

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

(Continued)

*Primary Examiner* — Elvis O Price

(57) ABSTRACT

Two or more vapor-liquid separators are used in a process for removing at least one non-condensable gas from a crude alcohol mixture prepared by hydrogenating alkanoic acid and/or esters thereof. The vapor-liquid separators may comprise flashers or knock-out pots and are suitable for removing non-condensable gas, including those gases that are dissolved in the liquid. The multiple vapor-liquid separators may be in series prior to any separation of organic components. In addition, there may be a vapor-liquid separator before and after a distillation column for treating the feed to the column.

12 Claims, 4 Drawing Sheets

(56) References Cited

U.S. PATENT DOCUMENTS

| | | | |
|---|---|---|---|
| 5,821,111 | A | 10/1998 | Gaady et al. |
| 5,993,610 | A | 11/1999 | Berg |
| 6,121,498 | A | 9/2000 | Tustin et al. |
| 6,143,930 | A | 11/2000 | Singh et al. |
| 6,232,352 | B1 | 5/2001 | Vidalin et al. |
| 6,294,703 | B1 | 9/2001 | Hara et al. |
| 6,375,807 | B1 | 4/2002 | Nieuwoudt et al. |
| 6,509,180 | B1 | 1/2003 | Verser et al. |
| 6,627,770 | B1 | 9/2003 | Cheung et al. |
| 6,657,078 | B2 | 12/2003 | Scates et al. |
| 6,685,754 | B2 | 2/2004 | Kindig et al. |
| 6,693,213 | B1 | 2/2004 | Kolena et al. |
| 6,723,886 | B2 | 4/2004 | Allison et al. |
| 6,906,228 | B2 | 6/2005 | Fischer et al. |
| 6,927,048 | B2 | 8/2005 | Verser et al. |
| 7,005,541 | B2 | 2/2006 | Cheung et al. |
| 7,074,603 | B2 | 7/2006 | Verser et al. |
| 7,115,772 | B2 | 10/2006 | Picard et al. |
| 7,208,624 | B2 | 4/2007 | Scates et al. |
| 7,297,236 | B1 | 11/2007 | Vander Griend et al. |
| 7,351,559 | B2 | 4/2008 | Verser et al. |
| 7,399,892 | B2 | 7/2008 | Rix et al. |
| 7,507,562 | B2 | 3/2009 | Verser et al. |
| 7,553,397 | B1 | 6/2009 | Colley et al. |
| 7,572,353 | B1 | 8/2009 | Vander et al. |
| 7,601,865 | B2 | 10/2009 | Verser et al. |
| 7,608,744 | B1 | 10/2009 | Johnston et al. |
| 7,682,812 | B2 | 3/2010 | Verser et al. |
| 7,732,173 | B2 | 6/2010 | Mairal et al. |
| 7,744,727 | B2 | 6/2010 | Blum et al. |
| 7,863,489 | B2 | 1/2011 | Johnston et al. |
| 7,884,253 | B2 | 2/2011 | Stites et al. |
| 7,888,082 | B2 | 2/2011 | Verser et al. |
| 2006/0019360 | A1 | 1/2006 | Verser et al. |
| 2007/0270511 | A1 | 11/2007 | Melnichuk et al. |
| 2008/0135396 | A1 | 6/2008 | Blum |
| 2008/0193989 | A1 | 8/2008 | Verser et al. |
| 2009/0014313 | A1 | 1/2009 | Lee et al. |
| 2009/0023192 | A1 | 1/2009 | Verser et al. |
| 2009/0069609 | A1 | 3/2009 | Kharas et al. |
| 2009/0081749 | A1 | 3/2009 | Verser et al. |
| 2009/0166172 | A1 | 7/2009 | Casey et al. |
| 2009/0281354 | A1 | 11/2009 | Mariansky et al. |
| 2009/0318573 | A1 | 12/2009 | Stites et al. |
| 2010/0029980 | A1 | 2/2010 | Johnston et al. |
| 2010/0029995 | A1 | 2/2010 | Johnston et al. |
| 2010/0030001 | A1 | 2/2010 | Chen et al. |
| 2010/0030002 | A1 | 2/2010 | Johnston et al. |
| 2010/0121114 | A1 | 5/2010 | Johnston et al. |
| 2010/0197485 | A1 | 8/2010 | Johnston et al. |
| 2011/0082322 | A1 | 4/2011 | Jevtic et al. |

FOREIGN PATENT DOCUMENTS

| | | |
|---|---|---|
| EP | 2060555 | 5/2009 |
| EP | 2069269 | 6/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| WO | WO 83/03409 | 10/1983 |
| WO | WO 2008/040980 | 4/2008 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2010/055285 | 5/2010 |
| WO | WO 2011/097193 | 8/2011 |
| WO | WO 2011/140468 | 11/2011 |

OTHER PUBLICATIONS

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

VAPOR SEPARATION IN ALCOHOL PRODUCTION

FIELD OF THE INVENTION

The present invention relates generally to processes for producing alcohols, such as ethanol and, in particular, to processes for separating vapors such as non-condensable gas from reaction mixtures resulting from the hydrogenation of alkanoic acid.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as biofuels. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

Excess of hydrogen is used to increase the yield of ethanol production in converting carbonaceous feedstock into low-molecular weight alcohols. Due to the use of excess amounts of hydrogen, it is beneficial to recycle the unreacted hydrogen back to the reactor. However, additional gases, such as methane, ethane, nitrogen, carbon monoxide, and carbon dioxide, which would build up in the reactor when hydrogen is recycled, are also formed during the reaction.

EP2060555 describes hydrogenating esters to alcohols and separates a hydrogen gas recycle stream in an alcohol separation zone.

EP2069269 describes hydrogenating acetic acid to hydrocarbons and a flasher for separating the crude mixture into a vapor fraction comprising carbon monoxide, carbon dioxide, methane, propane, water, and unreacted hydrogen. The vapor fraction is recycled to the reactor by passing through a carbon dioxide separator.

However, a need remains for improving the processes for controlling non-condensable gas from the hydrogenation of acetic acid to increase production of ethanol.

SUMMARY OF THE INVENTION

In a first embodiment, the present invention is directed to a process for recovering ethanol, comprising hydrogenating an acetic acid feed stream with excess hydrogen in a reactor in the presence of a catalyst to form a crude ethanol product; separating at least a portion of the crude ethanol product in a first flasher into a first vapor stream and an intermediate stream; separating at least a portion of the intermediate stream in a first distillation column to yield a first distillate comprising ethanol and at least one non-condensable gas and a first residue; separating at least a portion of the first distillate in a second flasher into a second vapor stream comprising at least one non-condensable gas and a liquid stream comprising ethanol; and recovering ethanol from the liquid stream.

In a second embodiment, the present invention is directed to a process for recovering ethanol, comprising hydrogenating an alkanoic acid and/or ester thereof with excess hydrogen in the presence of a catalyst to form a crude ethanol product; separating at least a portion of the crude ethanol product in a first flasher into a first vapor stream and an intermediate stream comprising at least one non-condensable gas; separating at least a portion of the intermediate stream in a second flasher into a second vapor stream and a liquid stream; separating at least a portion of the liquid stream in a first distillation column into a first distillate comprising ethanol and a second residue comprising a substantial portion of water fed to the first distillation column; and recovering ethanol from the first distillate.

In a third embodiment, the present invention is directed to a process for recovering ethanol, comprising hydrogenating an alkanoic acid and/or ester thereof with excess hydrogen in the presence of a catalyst to form a crude ethanol product; separating at least a portion of the crude ethanol product in a first flasher into a first vapor stream and an intermediate stream comprising at least one non-condensable gas; separating at least a portion of the intermediate stream in a second flasher into a second vapor stream and a liquid stream; separating a portion of the liquid stream in a first distillation column to yield a first distillate comprising ethyl acetate and a first residue comprising ethanol, and water, wherein a majority of the ethanol in the intermediate stream that is fed to the column is removed in the first residue; and recovering ethanol from the first residue.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
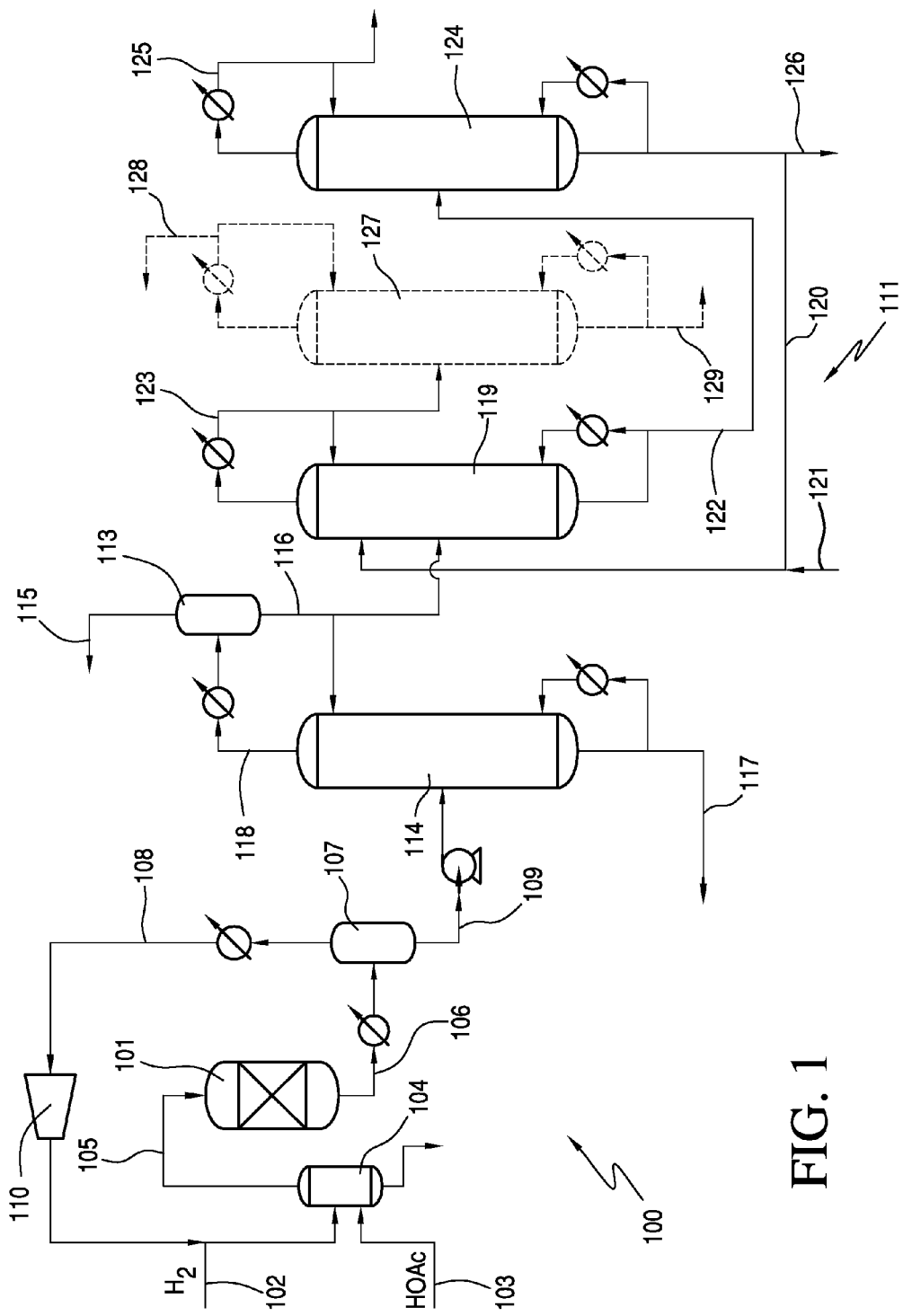
FIG. 1 is a schematic diagram of an ethanol recovery process having a low pressure flasher on the overhead of a column in a four column system in accordance with one embodiment of the present invention.

The present invention relates to processes for recovering ethanol produced by a hydrogenation process comprising hydrogenating alkanoic acid, such as acetic acid, in the presence of a catalyst. The hydrogenation process may use an excess molar amount of hydrogen. In addition, other non-condensable gases, such as carbon monoxide, carbon dioxide, methane, ethane, and nitrogen may be present in the crude ethanol product. Embodiments of the present invention recover ethanol from the crude ethanol product while separating out the non-condensable gases. The non-condensable gases, especially hydrogen, may be recycled to the reactor.

In one embodiment, two or more vapor portions of the crude ethanol product are separated by two or more vapor-liquid separators, i.e. flashers or knock-out pots. In these separators, gravity causes the liquid portion to collect in the bottom of the vessel, thereby allowing the liquid portion to be withdrawn and further separated. For purposes of the present invention, exemplary vapor-liquid separators used in the present invention are flashers. Flashers are vessels in which varying pressure and/or temperature may allow components, including ethanol and non-condensable gases, to be separated.

In some embodiments, the two or more flashers may be consecutive, while in other embodiments, the multiple flashers may be separated by one or more distillation columns. In some embodiments, some of the non-condensable gases may form in the distillation columns. Advantageously, the use of two or more flashers allows separation of the non-condensable gases that become dissolved in the liquid portions. Embodiments of the present invention beneficially may be used in applications for recovering ethanol on an industrial scale.

The hydrogenation of alkanoic acids to alcohols, such as acetic acid to form ethanol and water, may be represented by the following reaction:

$$R-COOH + 2H_2 \rightarrow R-COH + H_2O \qquad I$$

The hydrogenation of acetic acid forms equal molar ratios of ethanol and water. Although the reaction consumes two moles of hydrogen per mole of acetic acid to produce one mole of ethanol, the actual molar ratio of hydrogen to acetic acid in the feed stream may vary from about 100:1 to 2:1, e.g., from 50:1 to 4:1, or from 20:1 to 8:1. Most preferably, the molar ratio of hydrogen to acetic acid is greater than 2:1, e.g., greater than 4:1 or greater than 8:1. When excess of hydrogen is used, thermal decomposition of acetic acid, water-gas shift reaction and ethanol dehydration occur and form undesirable byproducts, such as methane, ethane, carbon monoxide and carbon dioxide, as shown below:

$$CH_3COOH \rightarrow CH_4 + CO_2 \qquad II$$

$$CO_2 + H_2 \leftrightarrow CO + H_2O \qquad III$$

$$CH_3CH_2OH \rightarrow CH_2=CH_2 + H_2O \qquad IV$$

$$CH_2=CH_2 + H_2 \rightarrow CH_3CH_3 \qquad V$$

Some of these byproduct gases, also referred to as non-condensable gases, may be harmful to certain types of hydrogenation catalysts and may lead to the formation of further impurities in the ethanol. Advantageously, the multiple vapor-liquid separators of the present invention may allow recovery of a hydrogen enriched stream and a purging a stream that comprises these byproduct gases. A hydrogen enriched stream refers to a stream in which the mole fraction of hydrogen is at least 50%, e.g., at least 75% or at least 90%.

To remove the byproduct gases, the crude ethanol product is passed through a first flasher to yield a first vapor portion and a first liquid portion. The first vapor portion, preferably enriched in hydrogen, may be recycled to the reactor as necessary to maintain pressure in the reactor and recycle excess hydrogen. The first liquid portion may contain dissolved non-condensable gases, such as carbon monoxide, carbon dioxide, methane, ethane, nitrogen, and/or hydrogen. In one embodiment, prior to removing at least one organic compound or water from the crude ethanol product, the present invention may pass a portion of first liquid portion to a second flasher. The second flasher removes the dissolved non-condensable gases and yields a second vapor portion. Without being bound by theory, carbon monoxide, carbon dioxide, methane, ethane and/or nitrogen may be dissolved in the first liquid portion and separated in the second flasher. The second vapor portion may have a mole fraction of hydrogen of less than 50%, e.g., less than 40% or less than 35%. Because these non-condensable gases may be less desirable to be recycled to the reactor than the hydrogen rich first vapor portion, the second vapor portion, or a fraction thereof, may be purged as necessary. Additional flashers may be used as necessary to further remove the non-condensable gases.

In another embodiment, after removing at least one organic or water from the crude ethanol product, a vapor portion comprising ethanol passes through a second flasher to remove non-condensable gases.

The multiple flashers may comprise at least one high pressure flasher and one low pressure flasher. Preferably, the low pressure flasher may operate at temperature and/or pressure that is less than the high pressure flasher. In one embodiment, the crude ethanol product may be initially separated in high pressure flasher followed by the low pressure flasher. Preferably, the low pressure flasher may remove dissolved non-condensable gases.

The high pressure flasher preferably operates at a temperature from 50° C. to 500° C., e.g., from 70° C. to 400° C. or from 100° C. to 350° C. In one embodiment, the pressure of high pressure flasher preferably is from 50 kPa to 2000 kPa, e.g., from 75 kPa to 1500 kPa or from 100 to 1000 kPa. Preferably, the high pressure flasher operates at a pressure and/or temperature that is less than the hydrogenation reactor. The low pressure flasher may operate at a temperature of from 20° C. to 250° C., e.g., from 30° C. to 225° C. or from 60° C. to 200° C. The pressure of low pressure flasher may be from 0.1 kPa to 1000 kPa, e.g., from 0.1 kPa to 500 kPa or from 10 kPa to 200 kPa. In one embodiment, the low pressure flasher may be operated under vacuum conditions.

In one embodiment, low pressure flasher may operate at a lower temperature and/or pressure than high pressure flasher. For temperatures, the temperature of low pressure flasher preferably is at least 50° C. lower than high pressure flasher, e.g., at least 75° C. lower or at least 100° C. lower. Low pressure flasher may be at least 50 kPa lower than high pressure flasher, e.g., at least 100 kPa lower or at least 200 kPa lower.

Hydrogenation Process

The process of the present invention may be used with any hydrogenation process for producing ethanol, preferably with ethanol produced by acetic acid hydrogenation. The materials, catalyst, reaction conditions, and separation are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259 and 4,994,608, the entire disclosures of which are incorporated herein by reference. Optionally, the production of ethanol may be integrated with such methanol carbonylation processes.

As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507, 562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884, 253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycled gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa, e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g from 500 $hr^{-1}$ to 30,000 $hr^{-1}$ from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal, or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. Most preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another, or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal is preferably from 0.05 to 4 wt. %, e.g., from 0.1 to 3 wt. %, or from 0.1 to 2 wt. %.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry; and packing density of about 0.352 $g/cm^3$ (22 $lb/ft^3$).

A preferred silica/alumina support material is KA-160 silica spheres from Süd-Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour, or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition, excluding non-condensable gases, comprising from 5 to 70 wt. % ethanol and from 5 to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %.

Ethyl acetate may also be produced during the hydrogenation of acetic acid, or through side reactions and may be present, for example, in amounts ranging from 0 to 20 wt. %, e.g., from 0 to 15 wt. %, from 1 to 12 wt. % or from 3 to 10 wt. %. In addition, acetaldehyde may be produced through side reactions, and may be present, for example, in amounts ranging from 0 to 10 wt. %, e.g., from 0 to 3 wt. %, from 0.1 to 3 wt. % or from 0.2 to 2 wt. %. Other components, such as, for example, alcohols, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be present in an amount from 0.1 to 10 wt. %, e.g., from 0.1 to 6 wt. %, or from 0.1 to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Ethanol Purification

Ethanol may be recovered using several separation processes. FIGS. 1-4 show a reaction zone 100 of a hydrogenation system suitable for the hydrogenation of acetic acid to form ethanol and a purification zone 111 suitable for the purification of ethanol produced by the hydrogenation of acetic acid according to one embodiment of the present invention. Reaction zone 100 comprises a reactor 101, hydrogen feed line 102 and acetic acid feed line 103. Hydrogen and acetic acid are fed to a vaporizer 104 via lines 102 and 103, respectively, to create a vapor feed stream in line 105 that is directed to reactor 101. Trace amount of nitrogen also may be present in one or both of the feed streams. In one embodiment, lines 102 and 103 may be combined and jointly fed to the vaporizer 104. The temperature of the vapor feed stream in line 105 is preferably from 100° C. to 350° C., e.g., from 120° C. to 310° C. or from 150° C. to 300° C. Any feed that is not vaporized is removed from vaporizer 104, as shown, and may be recycled thereto. In addition, although line 105 is shown as being directed to the top of reactor 101, line 105 may be directed to the side, upper portion, or bottom of reactor 101.

Reactor 101 contains the catalyst that is used in the hydrogenation of the carboxylic acid, preferably acetic acid. During the hydrogenation process, a crude ethanol product is withdrawn, preferably continuously, from reactor 101 via line 106. The crude ethanol product may be condensed and fed to a first flasher 107, which is a high pressure flasher. First flasher 107 provides a vapor stream 108 and a liquid stream 109. Vapor stream 108 may be returned to reactor 101 and recompressed as necessary via compressor 110.

Vapor stream 108 is a hydrogen enriched stream. In one exemplary embodiment, vapor stream 108 contains unreacted hydrogen in an amount between 90 to 100 mol. %, e.g., between 92 to 98 mol. %, or between 93 to 97 mol. % and contains by-product gases in an amount less than 10 mol. %, e.g., less than 5 mol. %, less than 3 mol. %, or less than 1 mol. %. In one embodiment, the byproduct gases are selected from the group consisting of methane, ethane, carbon dioxide, carbon monoxide, nitrogen, and mixtures thereof. Methane concentration may be less than 3 mol. %, e.g., less than 1.5 mol. % or less than 1.2 mol. %. Ethane concentration may be less than 3 mol. %, e.g., less than 1 mol. % or less than 0.8 mol. %. Carbon dioxide concentration may be less than 3 mol. %, e.g., less than 0.8 mol. % or less than 0.5 mol. %. Carbon monoxide concentration may be less than 2 mol. %, e.g., less than 0.3 mol. %, or less than 0.2 mol. %. Nitrogen concentration may be less than 2 mol. %, e.g., less than 0.4 mol. %, or less than 0.3 mol. %.

Figure 2:
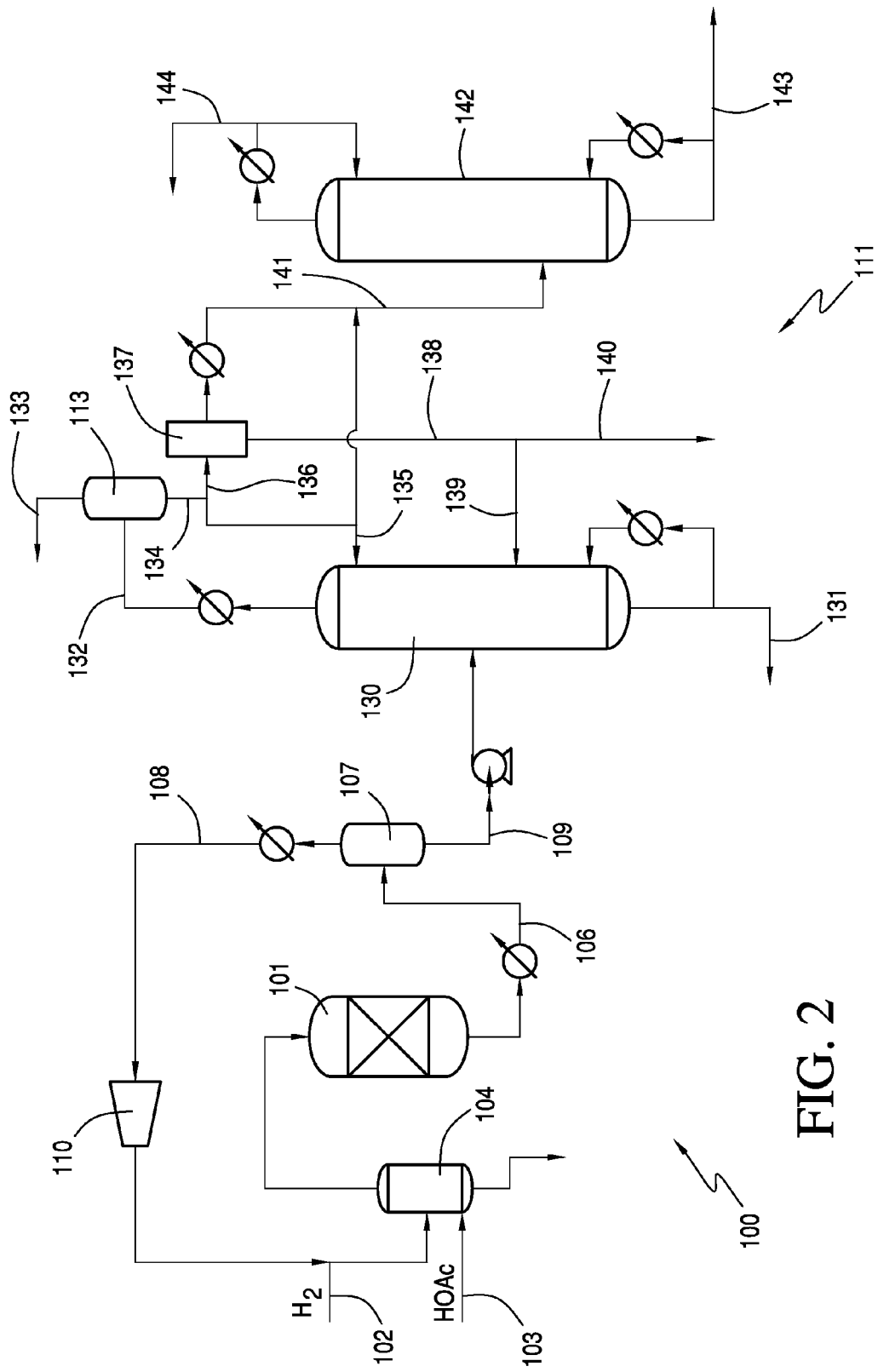
FIG. 2 is a schematic diagram of an ethanol recovery process having a low pressure flasher on the overhead of a column in a two column system in accordance with one embodiment of the present invention.

In FIGS. 1 and 2, liquid stream 109 is withdrawn from first flasher 107 and introduced to a distillation column. The contents of liquid stream 109 typically will be substantially similar to the product obtained directly from the reactor, and may, in fact, also be characterized as a crude ethanol product. However, the feed composition in line 109 preferably has less hydrogen, carbon dioxide, methane or ethane than the crude ethanol product in line 106, which are removed by first flasher 107. In embodiments of the present invention at least one of the non-condensable gases is dissolved in liquid stream 109. Exemplary compositions of liquid stream 109, excluding non-condensable gases, are provided in Table 2.

TABLE 2

LIQUID STREAM 109 COMPOSITION

| | Conc. (wt. %) | Conc. (wt. %) | Conc. (wt. %) |
|---|---|---|---|
| Ethanol | 5 to 70 | 10 to 60 | 15 to 50 |
| Acetic Acid | 0.0001 to 90 | 5 to 80 | 15 to 70 |

TABLE 2-continued

LIQUID STREAM 109 COMPOSITION

|  | Conc. (wt. %) | Conc. (wt. %) | Conc. (wt. %) |
|---|---|---|---|
| Water | 5 to 35 | 5 to 30 | 10 to 30 |
| Ethyl Acetate | 0.0001 to 20 | 0.001 to 15 | 1 to 12 |
| Acetaldehyde | 0.0001 to 10 | 0.001 to 3 | 0.1 to 3 |
| Acetal | 0.0001 to 5 | 0.001 to 2 | 0.005 to 1 |
| Acetone | 0.0001 to 5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 109, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 106 or in liquid stream 109 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In FIG. 1, liquid stream 109 is further separated in a first distillation column 114, referred to as an "acid separation column," to produce a first distillate stream 118 and a first residue stream 117. In one embodiment, acetic acid, a portion of the water, and other heavy components, if present, are removed from the composition in line 109 and are withdrawn, preferably continuously, as first residue stream 117. Some or all of the residue may be returned and/or recycled back to reaction zone 100 via line 117. Recycling the acetic acid in line 117 to the vaporizer 104 may reduce the amount of heavies that need to be purged from vaporizer 104. Reducing the amount of heavies to be purged may improve efficiencies of the process while reducing byproducts.

Ethanol and water may be separated in the first distillate stream 118, along with light organics, such as ethyl acetate, acetaldehyde, and/or diethyl acetal. Dissolved non-condensable gases are also concentrated in first distillate 118. First distillate 118 may be condensed and introduced to a second flasher 113. Second flasher 113 may be a low pressure flasher that operates at a lower pressure and/or temperature than first flasher 107. In one embodiment, the first flasher 107 and second flasher 113 may be operated at substantially the same temperature and/or pressure. Second flasher 113 produces a second vapor stream 115 and a second liquid stream 116. Second vapor stream 115 contains less hydrogen, based on molar fraction, than first vapor stream 108. Thus, to prevent recycling non-condensable gases that may be harmful to some hydrogenation catalyst, in particular carbon monoxide and dioxide, second vapor stream 115 may be purged from the system. When second vapor stream 115 is recycled, the stream may be compressed together with first vapor stream 108 and fed to vaporizer 104. In some embodiments, second vapor stream 115 may be introduced directly to vaporizer 104 without further compression.

Second liquid stream 116 may have less dissolved non-condensable gases than liquid stream 109 and preferably has substantially no dissolved non-condensable gases. In one embodiment, the dissolved non-condensable gases, such as hydrogen, methane, ethane, carbon monoxide, carbon dioxide and/or nitrogen, are present in liquid stream 116 in a concentration from 0.00001 to 0.1 wt. %, e.g., 0.00001 to 0.001 wt. % or 0.00001 to 0.0001 wt. %. Second liquid stream 116 may be further condensed and refluxed, for example, at a ratio of from 10:1 to 1:10, e.g., from 3:1 to 1:3 or from 1:2 to 2:1. Ethanol can then be recovered from second liquid stream 116 using one or more columns as described below.

When column 114 is operated under standard atmospheric pressure, the temperature of the residue exiting in line 117 preferably is from 95° C. to 120° C., e.g., from 110° C. to 117° C. or from 111° C. to 115° C. The temperature of the distillate exiting in line 118 preferably is from 70° C. to 110° C., e.g., from 75° C. to 95° C. or from 80° C. to 90° C. Column 114 preferably operates at ambient pressure. In other embodiments, the pressure of first column 114 may range from 0.1 kPa to 510 kPa, e.g., from 1 kPa to 475 kPa or from 1 kPa to 375 kPa.

Exemplary components of the distillate and residue compositions for first column 114 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

ACID COLUMN 114 (FIG. 1)

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, when any amount of acetal is detected in the feed that is introduced to the acid separation column 114, the acetal appears to decompose in the column such that less or even no detectable amounts are present in the distillate and/or residue.

To further separate second liquid stream 116, the stream is introduced to a second column 119, also referred to as the "light ends column," preferably in the middle part of column 119. Preferably second column 119 is an extractive distillation column, and an extraction agent is added thereto via lines 120 and/or 121. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, second liquid stream 116 that is fed to the second column 119 comprises ethyl acetate, ethanol, and water. These compounds tend to form binary and ternary azeotropes, which decrease separation efficiency. As shown, in one embodiment the extraction agent comprises the third residue in line 120. Preferably, the recycled third residue in line 120 is fed to second column 119 at a point higher than second liquid stream 116. In one embodiment, the recycled third residue in line 120 is fed near the top of second column 119 or fed, for example, above the feed in line 116 and below the reflux line from the condensed overheads. In a tray column, the third residue in line 120 is continuously added near the top of the second column 119 so that an appreciable amount of the third residue is present in the liquid phase on all of the trays below. In another embodiment, the extraction agent is fed from a source outside of the process via line 121 to second column 119. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 119. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 120 and co-fed to the second column 119. The additional extraction agent may also be added separately to the second column 119. In one aspect, the extraction agent comprises an extraction agent, e.g., water, derived from an external source via line 121 and none of the extraction agent is derived from the third residue.

Second column 119 may be a tray or packed column. In one embodiment, second column 119 is a tray column having from 5 to 70 trays, e.g., from 15 to 50 trays or from 20 to 45 trays. Although the temperature and pressure of second column 119 may vary, when at atmospheric pressure the temperature of the second residue exiting in line 122 preferably is from 60° C. to 90° C., e.g., from 70° C. to 90° C. or from 80° C. to 90° C. The temperature of the second distillate exiting in line 123 from second column 119 preferably is from 50° C. to 90° C., e.g., from 60° C. to 80° C. or from 60° C. to 70° C. Column 119 may operate at atmospheric pressure. In other embodiments, the pressure of second column 119 may range from 0.1 kPa to 510 kPa, e.g., from 1 kPa to 475 kPa or from 1 kPa to 375 kPa. Exemplary components for the distillate and residue compositions for second column 119 are provided in Table 4 below. It should be understood that the distillate and residue may also contain other components, not listed, such as components in the feed.

TABLE 4

| SECOND COLUMN 123 (FIG. 1) | | | |
|---|---|---|---|
| | Conc. (wt. %) | Conc. (wt. %) | Conc. (wt. %) |
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the recycling of the third residue promotes the separation of ethyl acetate from the residue of the second column 119. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 119, the weight ratio of ethyl acetate in the second residue to ethyl acetate in the second distillate approaches zero.

The weight ratio of ethanol in the second residue 122 to second distillate 123 preferably is at least 3:1, e.g., at least 6:1, at least 8:1, at least 10:1 or at least 15:1. All or a portion of the third residue 120 is recycled to the second column 119. In one embodiment, all of the third residue 120 may be recycled until the process reaches a steady state and then a portion of the third residue 120 is recycled with the remaining portion being purged from the system via line 126. The composition of the second residue 122 will tend to have lower amounts of ethanol than when the third residue 120 is not recycled. As the third residue 120 is recycled, the composition of the second residue 122, as provided in Table 4, comprises less than 30 wt. % of ethanol, e.g., less than 20 wt. % or less than 15 wt. %. The majority of the second residue 122 preferably comprises water. Notwithstanding this effect, the extractive distillation step advantageously also reduces the amount of ethyl acetate that is sent to the third column 124, which is highly beneficial in ultimately forming a highly pure ethanol product.

As shown, the second residue 122 from second column 119, which comprises ethanol and water, is fed to third column 124, also referred to as the "product column." More preferably, the second residue in line 122 is introduced in the lower part of third column 124, e.g., lower half or lower third. Third column 124 recovers ethanol, which preferably is substantially pure with respect to organic impurities and other than the azeotropic water content, as the distillate in line 125. The distillate of third column 125 preferably is refluxed as shown in FIG. 1, for example, at a reflux ratio of from 1:10 to 10:1, e.g., from 1:3 to 3:1 or from 1:2 to 2:1. The third residue in line 120, which comprises primarily water, preferably is returned to the second column 119 as an extraction agent as described above. In one embodiment, a first portion of the third residue in line 120 is recycled to the second column and a second portion is purged and removed from the system via line 126. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Although FIG. 1 shows third residue 120 being directly recycled to second column 119, third residue 120 may also be returned indirectly, for example, by storing a portion or all of the third residue 120 in a tank (not shown) or treating the third residue 120 to further separate any minor components such as aldehydes, higher molecular weight alcohols, or esters in one or more additional columns (not shown).

Third column 124 is preferably a tray column as described above and operates at atmospheric pressure or optionally at pressures above or below atmospheric pressure. The temperature of the third distillate exiting in line 125 preferably is from 60° C. to 110° C., e.g., from 70° C. to 100° C. or from 75° C. to 95° C. The temperature of the third residue in line 120 preferably is from 70° C. to 115° C., e.g., from 80° C. to 110° C. or from 85° C. to 105° C. Exemplary components of the distillate and residue compositions for third column 124 are provided in Table 5 below. It should be understood that the distillate and residue may also contain other components, not listed, such as components in the feed.

TABLE 5

THIRD COLUMN 124 (FIG. 1)

|  | Conc. (wt. %) | Conc. (wt. %) | Conc. (wt. %) |
| --- | --- | --- | --- |
| Distillate |  |  |  |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <12 | 0.0001 to 0.1 | 0.005 to 0.05 |
| Diethyl Acetal | <12 | 0.0001 to 0.05 | 0.005 to 0.025 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 120 is withdrawn from third column 124 at a temperature higher than the operating temperature of the second column 119. Preferably, the third residue in line 120 is integrated to heat one or more other streams or is reboiled prior to be returned to the second column 119.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns in the system. Preferably at least one side stream is used to remove impurities from the third column 124. The impurities may be purged and/or retained within the system.

The third distillate in line 125 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 119, the second distillate preferably is refluxed as shown in FIG. 1, optionally at a reflux ratio of 1:10 to 10:1, e.g., from 1:5 to 5:1 or from 1:3 to 3:1. The second distillate in line 123 may be purged or recycled to the reaction zone. In one embodiment, the second distillate in line 123 is further processed in an optional fourth column 127, also referred to as the "acetaldehyde removal column." In optional fourth column 127 the second distillate 123 is separated into a fourth distillate, which comprises acetaldehyde, in line 128 and a fourth residue, which comprises ethyl acetate, in line 129. The fourth distillate preferably is refluxed at a reflux ratio of from 1:20 to 20:1, e.g., from 1:15 to 15:1 or from 1:10 to 10:1, and a portion of the fourth distillate 128 is returned to the reaction zone 100. For example, the fourth distillate may be combined with the acetic acid feed, added to the vaporizer 104, or added directly to reactor 101. The fourth distillate 128 preferably is co-fed with the acetic acid in feed line 103 to vaporizer 104. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of optional fourth column 127 may be purged via line 129. The fourth residue 129 primarily comprises ethyl acetate and ethanol, which may be suitable for use as a solvent mixture or in the production of esters. In one preferred embodiment, the acetaldehyde is removed from the second distillate 123 in fourth column 127 such that no detectable amount of acetaldehyde is present in the residue 129.

Optional fourth column 127 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 127 may operate at a pressure that is higher than the pressure of the other columns.

The temperature of the fourth distillate exiting in line 128 preferably is from 60° C. to 110° C., e.g., from 70° C. to 100° C. or from 75° C. to 95° C. The temperature of the residue in line 129 preferably is from 70° C. to 115° C., e.g., from 80° C. to 110° C. or from 85° C. to 110° C. Exemplary components of the distillate and residue compositions for optional fourth column 127 are provided in Table 6 below. It should be understood that the distillate and residue may also contain other components, not listed, such as components in the feed.

TABLE 6

OPTIONAL FOURTH COLUMN 127 (FIG. 1)

|  | Conc. (wt. %) | Conc. (wt. %) | Conc. (wt. %) |
| --- | --- | --- | --- |
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

Returning to first flasher 107, in another exemplary embodiment shown in FIG. 2, ethanol may be recovered using two columns with an intervening water separation. The second flasher 113 is located at the overhead of the first column 130 in FIG. 2.

In an embodiment of the invention shown in FIG. 2, liquid stream 109 is introduced in the middle or lower portion of a first column 130, also referred to as acid-water column. For purposes of convenience, the columns in each exemplary separation process, may be referred as the first, second, third, etc., columns, but it is understood that first column 114 in FIG. 1 operates differently than the first column 130 of FIG. 2. In one embodiment, no entrainers are added to first column 130. In FIG. 2, first column 130, water and unreacted acetic acid, along with any other heavy components, if present, are removed from liquid stream 109 and are withdrawn, preferably continuously, as a first residue in line 131. Preferably, a substantial portion of the water in the crude ethanol product that is fed to first column 130 may be removed in the first residue 131, for example, up to about 90% of the water from the crude ethanol product, and more preferably up to about 75%.

First column 130 also forms a first distillate, which is withdrawn in line 132. First distillate 132 comprises ethanol, light organics, and dissolved non-condensable gases. Dissolved non-condensable gases are also concentrated in first distillate 132. First distillate 132 may be condensed and introduced to a second flasher 113. As indicated above, second flasher 113 is a low pressure flasher that operates at a lower pressure and/or temperature than first flasher 107. Second flasher 113 produces a second vapor stream 133 and a second liquid stream 134. Second vapor stream 133 contains less hydrogen, based on molar fraction, than first vapor stream 108. As discussed above, second vapor stream 133 may be recycled to reactor 101 or purged as necessary.

Second liquid stream 134 may have less dissolved non-condensable gases than liquid stream 109 and preferably has substantially no dissolved non-condensable gases. In one embodiment, the dissolved non-condensable gases, such as hydrogen, methane, ethane, carbon monoxide, carbon dioxide and/or nitrogen, are present in second liquid stream 134 in a concentration from 0.00001 to 0.1 wt. %, e.g., 0.00001 to 0.001 wt. % or 0.00001 to 0.0001 wt. %.

Second liquid stream 134 also comprises water, in addition to ethanol and other organics. In terms of ranges, the concentration of water in second liquid stream 134 preferably is from 4 wt. % to 38 wt. %, e.g., from 7 wt. % to 32 wt. %, or from 7 to 25 wt. %. A portion of second liquid stream in line 135 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 130. The condensed portion of the first distillate 134 may also be fed to a second column 142 via line 135.

The remaining portion of second liquid stream 134 is fed via line 136 to a water separation unit 137. Water separation unit 137 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separation unit 137 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separation unit 137 may remove at least 95% of the water from the portion of second liquid stream 134, and more preferably from 99% to 99.99% of the water from the second liquid stream, in a water stream 138. All or a portion of water stream 138 may be returned to column 130 in line 139, where the water preferably is ultimately recovered from column 130 in the first residue in line 131. Additionally or alternatively, all or a portion of water stream 138 may be purged via line 140. The remaining portion of second liquid stream exits the water separation unit 137 as ethanol mixture stream 141. Ethanol mixture stream 141 may have a low concentration of water of less than 10 wt. %, e.g., less than 6 wt. % or less than 2 wt. %.

When column 130 is operated under about 170 kPa, the temperature of the residue exiting in line 131 preferably is from 90° C. to 130° C., e.g., from 95° C. to 120° C. or from 100° C. to 115° C. The temperature of the distillate exiting in line 132 preferably is from 60° C. to 90° C., e.g., from 65° C. to 85° C. or from 70° C. to 80° C. In some embodiments, the pressure of first column 130 may range from 0.1 kPa to 510 kPa, e.g., from 1 kPa to 475 kPa or from 1 kPa to 375 kPa.

Exemplary components of ethanol mixture stream 141 and first residue in line 131 are provided in Table 7 below. It should also be understood that these streams may also contain other components, not listed, such as components derived from the feed.

TABLE 7

| FIRST COLUMN 130 WITH PSA (FIG. 2) | | | |
|---|---|---|---|
| | Conc. (wt. %) | Conc. (wt. %) | Conc. (wt. %) |
| Ethanol Mixture Stream | | | |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <1 | 0.001 to 0.5 | 0.005 to 0.05 |
| Acetal | <0.1 | <0.05 | <0.01 |
| Acetone | <0.05 | 0.001 to 0.03 | 0.01 to 0.025 |
| Residue | | | |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 141 is not returned or refluxed to first column 130. The condensed portion of the second liquid stream 134 may be combined with ethanol mixture stream 141 to control the water concentration fed to the second column 142. For example, in some embodiments second liquid stream 134 may be split into equal portions, while in other embodiments, all of second liquid stream 134 may be condensed or all of second liquid stream 134 may be processed in the water separation unit 137. In FIG. 2, the condensed portion in line 135 and ethanol mixture stream 141 are co-fed to second column 142. In other embodiments, the condensed portion in line 135 and ethanol mixture stream 141 may be separately fed to second column 142. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 142 in FIG. 2, also referred to as the "light ends column," removes ethyl acetate and acetaldehyde from the condensed distillate in line 135 and/or ethanol mixture stream 141. Ethyl acetate and acetaldehyde are removed as a second distillate in line 144 and ethanol is removed as the second residue in line 143. Second column 142 may be a tray column or packed column. In one embodiment, second column 142 is a tray column having from 5 to 70 trays, e.g., from 15 to 50 trays or from 20 to 45 trays.

Second column 142 operates at a pressure ranging from 0.1 kPa to 510 kPa, e.g., from 10 kPa to 450 kPa or from 50 kPa to 350 kPa. Although the temperature of second column 142 may vary, when at about 20 kPa to 70 kPa, the temperature of the second residue exiting in line 143 preferably is from 30° C. to 75° C., e.g., from 35° C. to 70° C. or from 40° C. to 65° C. The temperature of the second distillate exiting in line 144 preferably is from 20° C. to 55° C., e.g., from 25° C. to 50° C. or from 30° C. to 45° C.

The total concentration of water fed to second column 142 preferably is less than 10 wt. %, as discussed above. When condensed distillate in line 135 and/or ethanol mixture stream 141 comprises minor amounts of water, e.g., less than 1 wt. % or less than 0.5 wt. %, additional water may be fed to the second column 142 as an extractive agent in the upper portion of the column. A sufficient amount of water is preferably added via the extractive agent such that the total concentration of water fed to second column 142 is from 1 to 10 wt. % water, e.g., from 2 to 6 wt. %, based on the total weight of all components fed to second column 142. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate 144 and second residue 143 compositions for the second column 142 are provided in Table 8, below. It should be understood that the distillate 144 and residue 143 may also contain other components, not listed in Table 8.

TABLE 8

| SECOND COLUMN 142 (FIG. 2) | | | |
|---|---|---|---|
| | Conc. (wt. %) | Conc. (wt. %) | Conc. (wt. %) |
| Second Distillate | | | |
| Ethyl Acetate | 5 to 90 | 10 to 80 | 15 to 75 |
| Acetaldehyde | <5 | 0.005 to 2 | 0.01 to 1 |
| Ethanol | <45 | 0.001 to 40 | 0.01 to 35 |
| Water | <20 | 0.01 to 10 | 0.1 to 5 |
| Second Residue | | | |
| Ethanol | 80 to 99.5 | 85 to 99.5 | 90 to 99.5 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |

The second distillate in line 144, which comprises ethyl acetate and/or acetaldehyde, preferably is refluxed as shown in FIG. 2, for example, at a reflux ratio of from 1:30 to 30:1, e.g., from 1:10 to 10:1 or from 1:3 to 3:1. In one aspect, not shown, the second distillate 144 or a portion thereof may be returned to reaction zone 100. The ethyl acetate and/or acetaldehyde in the second distillate may be further reacted in hydrogenation reactor 101.

In optional embodiment, the second distillate in line 144, may be further separated to produce an acetaldehyde-containing stream and an ethyl acetate-containing stream using optional fourth column 127 of FIG. 1. This may allow a portion of either the resulting acetaldehyde-containing stream or ethyl acetate-containing stream to be recycled to reactor 101 while purging the other stream. The purge stream may be valuable as a source of either ethyl acetate and/or acetaldehyde.

Figure 3:
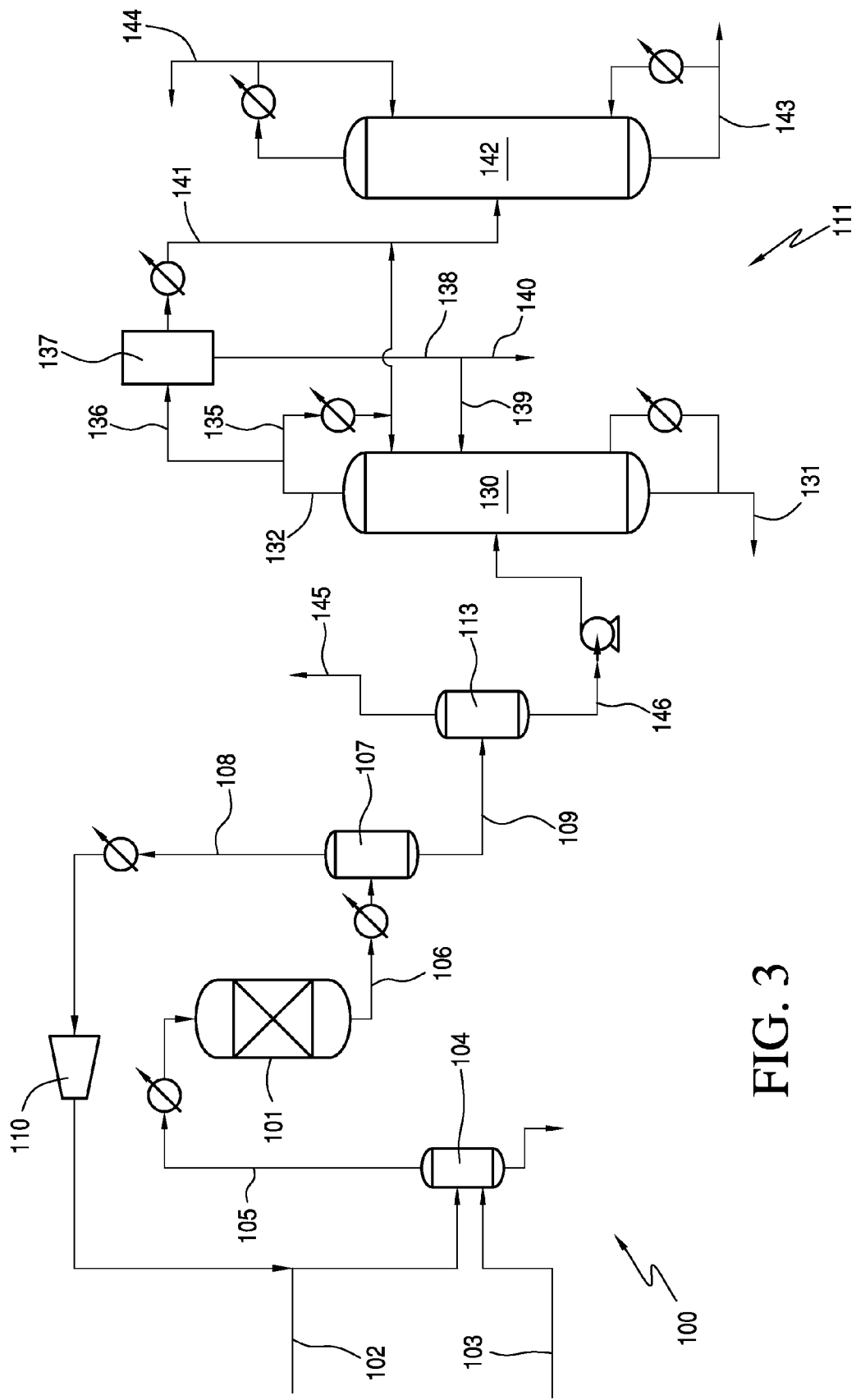
FIG. 3 is a schematic diagram of an ethanol recovery process having dual flashers in sequence for a two column system having an intervening water separation in accordance with one embodiment of the present invention.

In other embodiments of the present invention, the two or more vapor-liquid separators may be used prior to the separation of organics from the crude ethanol. Preferably dual flashers in sequence may be used. In FIG. 3, the second flasher 113 is positioned directly after the first flasher 107, and the first liquid stream 109, i.e. an intermediate stream, is introduced to second flasher 113. In one embodiment, first flasher 107 is a high pressure flasher and yields a first vapor stream 108 and a first liquid stream 109. Second flasher 113 is a low pressure flasher and yields a second vapor stream 145 and a second liquid stream 146. Second flasher 113 is a low pressure flasher that operates at a lower pressure and/or temperature than first flasher 107. Second vapor stream 145 contains less hydrogen, based on molar fraction, than first vapor stream 108. Vapor streams 108 and/145 may be recycled to reactor 101, and preferably at least vapor stream 108 is recycled. Second liquid stream 146 may have less dissolved non-condensable gases than liquid stream 109 and preferably has substantially no dissolved non-condensable gases. In one embodiment, the dissolved non-condensable gases, such as hydrogen, methane, ethane, carbon monoxide, carbon dioxide and/or nitrogen, are present in liquid stream 146 in a concentration from 0.00001 to 0.1 wt. %, e.g., 0.00001 to 0.001 wt. % or 0.00001 to 0.0001 wt. %.

As shown in FIG. 3, second liquid stream 146 is introduced to column 130. First distillate 132 is separated into a portion that is refluxed in line 135 and a portion that is fed to a water separation unit 137 in line 136. Ethanol is recovered using second column 142 as described above.

Figure 4:
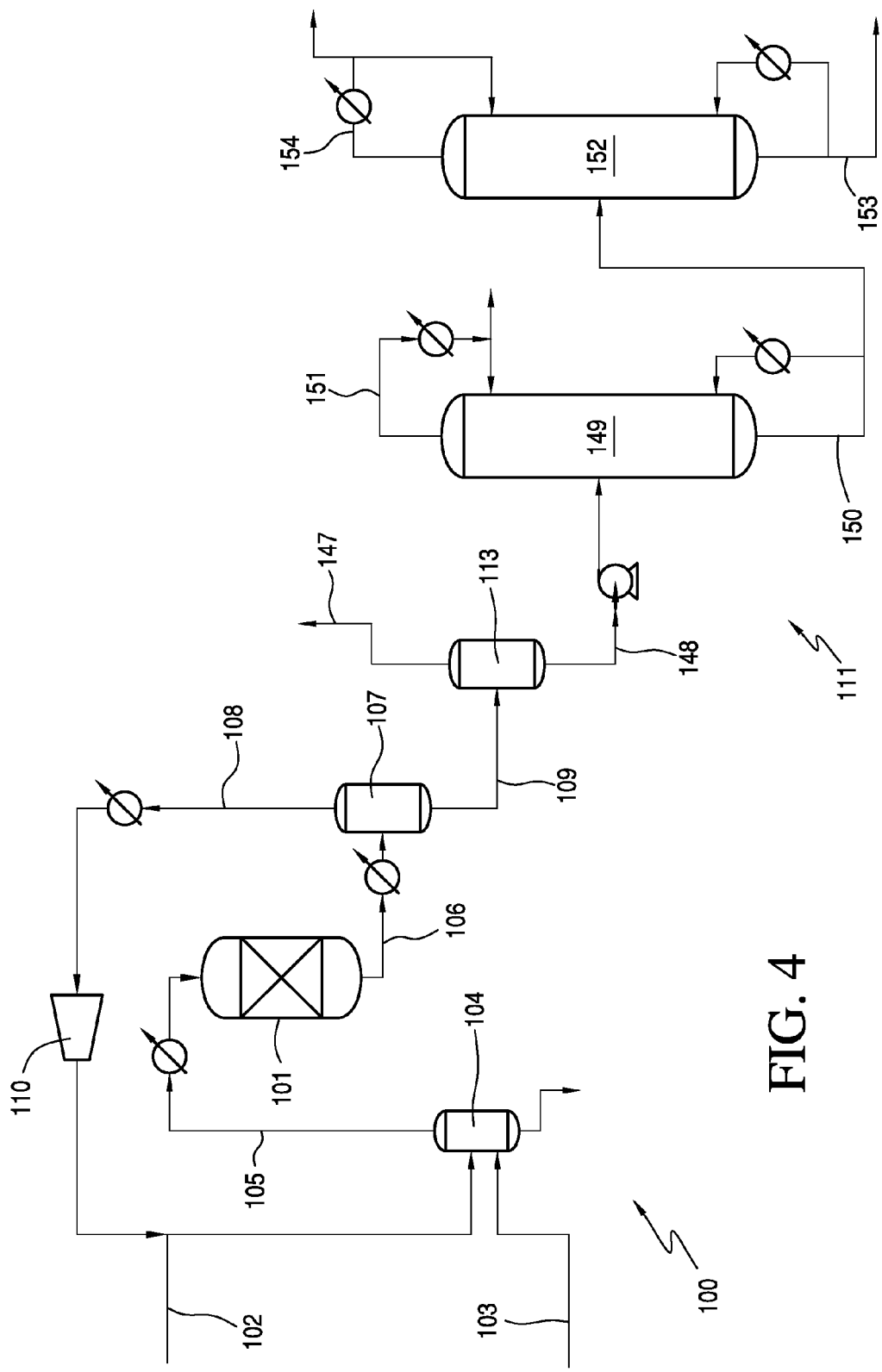
FIG. 4 is a schematic diagram of an ethanol recovery process having dual flashers in sequence for a two column system in accordance with one embodiment of the present invention.

Ethanol may also be recovered from second liquid stream 148 using an exemplary separation system shown in FIG. 4. Liquid stream 148 is introduced in the upper part of first column 149, e.g., upper half or upper third. In one embodiment, no entrainers are added to first column 149. In first column 149, a weight majority of the ethanol, water, acetic acid, and other heavy components, if present, are removed from liquid stream 148 and are withdrawn, preferably continuously, as residue in line 150. First column 149 also forms an overhead distillate, which is withdrawn in line 151, and which may be condensed and refluxed, for example, at a ratio of from 30:1 to 1:30, e.g., from 10:1 to 1:10 or from 1:5 to 5:1. The overhead distillate in stream 151 preferably comprises a weight majority of the ethyl acetate from liquid stream 148. The first distillate in line 151 is, for example, refluxed at a reflux ratio of from 1:30 to 30:1, e.g., from 1:10 to 10:1 or from 1:3 to 3:1. The first residue in line 150 preferably is refluxed as shown in FIG. 4, for example, at a reflux ratio of from 1:30 to 30:1, e.g., from 1:10 to 10:1 or from 1:3 to 3:1.

When column 149 is operated under about 170 kPa, the temperature of the residue exiting in line 150 preferably is from 70° C. to 155° C., e.g., from 90° C. to 130° C. or from 100° C. to 110° C. The base of column 149 may be maintained at a relatively low temperature by withdrawing a residue stream comprising ethanol, water, and acetic acid, thereby providing an energy efficiency advantage. The temperature of the distillate exiting in line 151 preferably at 170 kPa is from 75° C. to 100° C., e.g., from 75° C. to 83° C. or from 81° C. to 84° C. In some embodiments, the pressure of first column 149 may range from 0.1 kPa to 510 kPa, e.g., from 1 kPa to 475 kPa or from 1 kPa to 375 kPa. Exemplary components of the distillate and residue compositions for first column 149 are provided in Table 9 below. It should also be understood that the distillate and residue may also contain other components, not listed in Table 9.

TABLE 9

FIRST COLUMN 149 (FIG. 4)

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | <0.1 | 0.0001 to 0.05 | 0.005 to 0.025 |
| Acetal | <0.1 | 0.0001 to 0.05 | 0.005 to 0.025 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.01 to 35 | 0.1 to 30 | 0.2 to 25 |
| Water | 25 to 70 | 30 to 65 | 35 to 60 |
| Ethanol | 10 to 75 | 15 to 70 | 20 to 65 |

In an embodiment of the present invention, column 149 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 150 to water in the distillate in line 151 may be greater than 1:1, e.g., greater than 2:1. The weight ratio of ethanol in the residue to ethanol in the distillate may be greater than 1:1, e.g., greater than 2:1

The amount of acetic acid in the first residue 150 may vary depending primarily on the conversion in reaction zone 100. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate 151 preferably is substantially free of acetic acid, e.g., comprising less than 1000 ppm, less than 500 ppm or less than 100 ppm acetic acid. The distillate may be purged from the system or recycled in whole or part to first reaction zone 100. In some embodiments, the distillate 151 may be further separated, e.g., in a distillation column (not shown), into an acetaldehyde stream and an ethyl acetate stream. Either of these streams may be returned to the reaction zone 100 or separated from system as a separate product.

Some species, such as acetals, may decompose in first column 149 such that very low amounts, or even no detectable amounts, of acetals remain in the distillate or residue.

To recover ethanol, the residue in line 150 may be further separated in a second column 152, also referred to as an "acid separation column." An acid separation column may be used when the acetic acid concentration in the first residue is greater than 1 wt. %, e.g., greater than 5 wt. %. The first residue in line 150 is introduced to second column 152 preferably in the top part of column 152, e.g., top half or top third. Second column 152 yields a second residue in line 153 comprising acetic acid and water, and a second distillate in line 154 comprising ethanol. The second distillate in line 154, preferably is refluxed as shown in FIG. 4, for example, at a reflux ratio of from 1:30 to 30:1, e.g., from 1:10 to 10:1 or from 1:3 to 3:1. Second column 152 may be a tray column or packed column. In one embodiment, second column 152 is a tray column having from 5 to 150 trays, e.g., from 15 to 50 trays or from 20 to 45 trays. Although the temperature and pressure of second column 152 may vary, when at atmospheric pressure the temperature of the second residue exiting in line 153 preferably is from 95° C. to 130° C., e.g., from 100° C. to 125° C. or from 110° C. to 120° C. The temperature of the second distillate exiting in line 154 preferably is from 60° C. to 105° C., e.g., from 75° C. to 100° C. or from 80° C. to 100° C. The pressure of second column 152 may range from 0.1 kPa to 510 kPa, e.g., from 1 kPa to 475 kPa or from 1 kPa to 375 kPa. Exemplary components for the distillate and residue compositions for second column 152 are provided in Table 10 below. It should be understood that the distillate and residue may also contain other components, not listed in Table 10.

TABLE 10

SECOND COLUMN 152 (FIG. 4)

|  | Conc. (wt. %) | Conc. (wt. %) | Conc. (wt. %) |
|---|---|---|---|
| Second Distillate |  |  |  |
| Ethanol | 70 to 99.9 | 75 to 99.5 | 80 to 99.5 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 0.5 to 25 | 0.5 to 20 |
| Second Residue |  |  |  |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 154 to ethanol in the second residue in line 153 preferably is at least 35:1. In one embodiment, the weight ratio of water in the second residue 153 to water in the second distillate 154 is greater than 2:1, e.g., greater than 4:1 or greater than 6:1. In addition, the weight ratio of acetic acid in the second residue 155 to acetic acid in the second distillate 154 preferably is greater than 10:1, e.g., greater than 15:1 or greater than 20:1. Preferably, the second distillate in line 154 is substantially free of acetic acid and may only contain, if any, trace amounts of acetic acid. Preferably, the second distillate in line 154 contains substantially no ethyl acetate.

The remaining water from the second distillate in line 154 may be removed in further embodiments of the present invention. Depending on the water concentration, the ethanol product may be derived from the second distillate in line 154. Some applications, such as industrial ethanol applications, may tolerate water in the ethanol product, while other applications, such as fuel applications, may require an anhydrous ethanol. The amount of water in the distillate of line 154 may be closer to the azeotropic amount of water, e.g., at least 4 wt. %, preferably less than 20 wt. %, e.g., less than 12 wt. % or less than 7.5 wt. %. Water may be removed from the second distillate in line 154 using several different separation techniques as described herein. Particularly preferred techniques include the use of distillation column, membranes, adsorption units, and combinations thereof.

Some of the residues withdrawn from the exemplary separation systems may comprise acetic acid and water. Depending on the water and acetic acid concentration, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reaction zone 100. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 101, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The final ethanol product produced by the processes of the present invention may be taken from a stream that primarily comprises ethanol. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 11.

TABLE 11

| FINISHED ETHANOL COMPOSITIONS | | | |
|---|---|---|---|
| Component | Conc. (wt. %) | Conc. (wt. %) | Conc. (wt. %) |
| Ethanol | 75 to 99.9 | 80 to 99.5 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 11, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The columns shown in figures may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and two flashers are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for recovering ethanol, comprising:
   hydrogenating an acetic acid feed stream with excess hydrogen in a reactor in the presence of a catalyst to form a crude ethanol product;
   separating at least a portion of the crude ethanol product in a first flasher into a first vapor stream and an intermediate stream;
   separating at least a portion of the intermediate stream in a first distillation column to yield a first distillate comprising ethanol and at least one non-condensable gas and a first residue;
   separating at least a portion of the first distillate in a second flasher into a second vapor stream comprising at least one non-condensable gas and a liquid stream comprising ethanol; and
   recovering ethanol from the liquid stream.

2. The process of claim 1, wherein the first flasher is operated at a temperature ranging from 50° C. to 500° C. and wherein the second flasher is operated at a temperature ranging from 20° C. to 100° C.

3. The process of claim 1, wherein the first flasher is operated at a pressure ranging from 50 kPa to 5000 kPa and wherein the second flasher is operated at a pressure ranging from 0.1 kPa to 1000 k Pa.

4. The process of claim 1, wherein the first and second flashers are operated at similar pressures and/or temperatures.

5. The process of claim 1, wherein the liquid stream comprises substantially no hydrogen.

6. The process of claim 1, wherein the first distillate comprises ethanol and the first residue comprises acetic acid.

7. The process of claim 1, wherein the at least one non-condensable gas is selected from the group consisting of hydrogen, methane, ethane, nitrogen, carbon monoxide, and carbon dioxide.

8. The process of claim 1, wherein the first vapor stream is returned to the reactor.

9. The process of claim 1, wherein the second vapor stream is returned to the reactor.

10. The process of claim 1, further comprising
    separating at least a portion of the liquid stream in a second distillation column into a second distillate comprising ethyl acetate and a second residue comprising ethanol and water; and
    separating at least a portion of the second residue in a third distillation column into a third distillate comprising ethanol and a third residue comprising water.

11. The process of claim 10, wherein a portion of the third residue is returned to the second distillation column.

12. The process of claim 1, further comprising
    removing water from the liquid stream to yield an ethanol mixture stream comprising less than 10 wt. % water; and
    separating at least a portion of the liquid stream in a second distillation column into a second distillate comprising ethyl acetate and a second residue comprising ethanol.

* * * * *